(12) United States Patent
Curro et al.

(10) Patent No.: US 6,884,494 B1
(45) Date of Patent: *Apr. 26, 2005

(54) LAMINATE WEB

(75) Inventors: John J. Curro, Cincinnati, OH (US); Douglas H. Benson, W. Harrison, IN (US); John B. Strube, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/467,938

(22) Filed: Dec. 21, 1999

(51) Int. Cl.[7] .............................. B32B 3/02; B32B 3/26; B32B 5/26; B32B 27/02
(52) U.S. Cl. ...................... 428/196; 428/71; 428/158; 428/172; 428/196; 442/389; 442/392; 442/409
(58) Field of Search ................................. 428/131, 136, 428/137; 442/381, 389, 328, 394, 370, 378, 409, 373, 412, 392

(56) References Cited

U.S. PATENT DOCUMENTS

| | | | |
|---|---|---|---|
| 2,257,428 A | 9/1941 | Ruegenberg | 154/55 |
| 2,679,887 A | 6/1954 | Doyle et al. | 154/33.05 |
| 2,862,251 A | 12/1958 | Kalwaites | 19/161 |
| 2,896,692 A | 7/1959 | Villoresi | 154/33.05 |
| 3,081,500 A | 3/1963 | Griswold et al. | 19/161 |
| 3,081,512 A | 3/1963 | Griswold | 28/72 |
| 3,354,022 A | 11/1967 | Dettre et al. | |
| 3,485,706 A | 12/1969 | Evans | 161/72 |
| 3,542,634 A | 11/1970 | Such et al. | 161/88 |
| 3,574,109 A | 4/1971 | Yoshikawa | 161/128 |
| 3,597,299 A | 8/1971 | Thomas et al. | 161/57 |
| 3,681,182 A | 8/1972 | Kalwaites | 161/109 |
| 3,681,183 A | 8/1972 | Kalwaites | 161/109 |
| 3,695,967 A | 10/1972 | Ross | |

(Continued)

FOREIGN PATENT DOCUMENTS

| | | | |
|---|---|---|---|
| EP | 0 112 654 A2 | | 7/1984 |
| EP | A-207904 | * | 1/1987 |

(Continued)

*Primary Examiner*—Cheryl A. Juska
*Assistant Examiner*—Jenna-Leigh Befumo
(74) *Attorney, Agent, or Firm*—Angela Marie Stone; Roddy M. Bullock

(57) ABSTRACT

A laminate web is disclose, the laminate web comprising a first web, a second web joined to the first web at a plurality of discrete bond sites; and a third material disposed between at least a portion of the first and second nonwovens. The third material is apertured in regions adjacent the bond sites, such that the first and second nonwoven webs are joined through the apertures. In one embodiment an apertured laminate web is disclosed, having a first extensible web having a first elongation to break, and a second extensible web joined to the first extensible web at a plurality of bond sites, the second extensible web having a second elongation to break A third web material is disposed between the first and second nonwovens, the third web material having a third elongation to break which is less than both of the first or second elongations to break. In a further embodiment, an apertured laminate web is disclose, having first and second extensible webs being joined at a plurality of discrete bond sites and a third material disposed between the first and second nonwoven webs. The first and second nonwoven webs are in fluid communication via the apertures and have distinct regions being differentiated by at least one property selected from the group consisting of basis weight, fiber orientation, thickness, and density.

18 Claims, 10 Drawing Sheets

U.S. PATENT DOCUMENTS

| | | |
|---|---|---|
| 3,695,985 A | 10/1972 | Brock et al. ................. 161/129 |
| 3,728,203 A | 4/1973 | Taylor ............................ 161/39 |
| 3,800,364 A | 4/1974 | Kalwaites ..................... 19/161 |
| 3,855,046 A | 12/1974 | Hansen et al. |
| 3,860,003 A | 1/1975 | Buell |
| 3,881,987 A | 5/1975 | Benz ............................ 162/116 |
| 3,927,673 A | 12/1975 | Taylor |
| 3,929,135 A | 12/1975 | Thompson |
| 3,949,127 A | 4/1976 | Ostermeier et al. .......... 428/137 |
| 3,953,638 A | 4/1976 | Kemp ........................... 428/154 |
| 4,062,993 A | 12/1977 | Seward |
| 4,101,625 A | 7/1978 | Haley .......................... 264/287 |
| 4,116,892 A | 9/1978 | Schwarz ........................ 521/62 |
| 4,135,021 A | 1/1979 | Patchell et al. .............. 428/134 |
| 4,153,664 A | 5/1979 | Sabee ......................... 264/289 |
| 4,207,367 A | 6/1980 | Baker, Jr. .................... 428/171 |
| 4,223,059 A | 9/1980 | Schwarz ...................... 428/198 |
| 4,276,336 A | 6/1981 | Sabee ......................... 428/132 |
| 4,285,100 A | 8/1981 | Schwarz .................... 19/161.1 |
| 4,333,979 A | 6/1982 | Sciaraffa et al. ............ 428/179 |
| 4,342,314 A | 8/1982 | Radel et al. |
| 4,349,020 A | 9/1982 | Krikorian .................... 128/155 |
| 4,355,066 A | 10/1982 | Newman ..................... 428/198 |
| 4,404,052 A | 9/1983 | Persson et al. |
| 4,414,970 A | 11/1983 | Berry |
| 4,418,123 A | 11/1983 | Bunnelle et al. ............. 428/517 |
| 4,421,812 A | 12/1983 | Plant ........................... 428/152 |
| 4,522,863 A | 6/1985 | Keck et al. .................. 428/196 |
| 4,525,407 A | 6/1985 | Ness ............................ 428/138 |
| 4,573,991 A | 3/1986 | Pieniak et al. |
| 4,588,630 A | 5/1986 | Shimalla ..................... 428/131 |
| 4,600,620 A | 7/1986 | Lloyd et al. |
| 4,603,069 A | 7/1986 | Haq et al. ..................... 428/76 |
| 4,606,964 A | 8/1986 | Wideman .................... 428/152 |
| 4,609,518 A | 9/1986 | Curro et al. |
| 4,629,643 A | 12/1986 | Curro et al. |
| 4,657,802 A | 4/1987 | Morman |
| 4,695,278 A | 9/1987 | Lawson |
| 4,720,415 A | 1/1988 | Vander Wielen et al. |
| 4,741,944 A | 5/1988 | Jackson et al. .............. 428/152 |
| 4,758,297 A | 7/1988 | Calligarich .................. 156/251 |
| 4,797,310 A | 1/1989 | Barby et al. |
| 4,801,482 A | 1/1989 | Goggans et al. |
| 4,808,178 A | 2/1989 | Aziz et al. |
| 4,816,025 A | 3/1989 | Foreman |
| 4,840,829 A | 6/1989 | Suzuki et al. ................ 428/133 |
| 4,842,596 A | 6/1989 | Kielpikowski et al. |
| 4,847,134 A | 7/1989 | Fahrenkrug et al. ......... 428/138 |
| 4,891,258 A | 1/1990 | Fahrenkrug .................. 428/138 |
| 5,116,662 A | 5/1992 | Morman |
| 5,143,679 A | 9/1992 | Weber et al. ............. 264/288.8 |
| 5,151,092 A | 9/1992 | Buell et al. |
| 5,156,793 A | 10/1992 | Buell et al. ............... 264/288.8 |
| 5,167,897 A | 12/1992 | Weber et al. ............. 264/288.8 |
| 5,204,158 A | 4/1993 | Phillips et al. ............... 428/134 |
| 5,260,345 A | 11/1993 | DesMarais et al. |
| 5,268,224 A | 12/1993 | DesMarais et al. |
| 5,320,891 A | 6/1994 | Levy et al. ................... 428/108 |
| 5,338,766 A | 8/1994 | Phan et al. |
| 5,376,198 A | 12/1994 | Fahrenkrug et al. ......... 156/164 |
| 5,431,991 A | 7/1995 | Quantrille et al. ........... 428/109 |
| 5,451,219 A | 9/1995 | Suzuki et al. ................ 604/385 |
| 5,518,801 A | 5/1996 | Chappell et al. ............. 428/152 |
| 5,536,555 A | 7/1996 | Zelazoski et al. ........... 428/138 |
| 5,567,501 A | 10/1996 | Srinivasan et al. .......... 428/137 |
| 5,587,225 A | 12/1996 | Griesbach et al. |
| 5,595,567 A | 1/1997 | King et al. |
| 5,620,779 A | 4/1997 | Levy et al. |
| 5,623,888 A | 4/1997 | Zafiroglu ..................... 112/414 |
| 5,626,571 A | 5/1997 | Young et al. ................. 604/370 |
| 5,628,097 A | 5/1997 | Benson et al. ................. 28/165 |
| 5,635,290 A | 6/1997 | Stopper et al. |
| 5,658,639 A | 8/1997 | Curro et al. .................. 428/131 |
| 5,662,634 A | 9/1997 | Yamamoto et al. .......... 604/378 |
| 5,681,302 A | 10/1997 | Melbye et al. |
| 5,683,374 A | 11/1997 | Yamamoto et al. .......... 604/385 |
| 5,683,794 A | 11/1997 | Wadsworth et al. |
| 5,691,035 A | 11/1997 | Chappell et al. ............. 428/152 |
| 5,714,107 A | 2/1998 | Levy et al. ................... 264/289 |
| 5,733,822 A | 3/1998 | Gessner et al. |
| 5,804,021 A | 9/1998 | Abuto et al. ................. 156/252 |
| 5,830,555 A | 11/1998 | Srinivasan et al. .......... 428/137 |
| 5,846,232 A | 12/1998 | Serbiak et al. |
| 5,851,935 A | 12/1998 | Srinivasan et al. |
| 5,853,881 A | 12/1998 | Estey et al. |
| 5,891,544 A | 4/1999 | Chappell et al. ............... 428/76 |
| 5,906,879 A | 5/1999 | Huntoon et al. ............. 428/136 |
| 5,916,661 A | 6/1999 | Benson et al. ............... 428/131 |
| 5,919,411 A | 7/1999 | Rezai et al. .................. 264/154 |
| 6,015,605 A | 1/2000 | Tsujiyama et al. ........... 428/195 |
| 6,022,607 A | 2/2000 | James et al. ................. 428/131 |
| 6,025,050 A | 2/2000 | Srinivasan et al. .......... 428/137 |
| 6,027,593 A | 2/2000 | Lunt et al. |
| 6,054,202 A | 4/2000 | Takeuchi et al. ............. 428/167 |
| 6,057,024 A | 5/2000 | Mleziva et al. |
| 6,086,984 A | 7/2000 | DiMaggio, Jr. et al. |
| 6,106,925 A | 8/2000 | Palumbo ...................... 428/137 |
| 6,203,654 B1 | 3/2001 | McFall et al. |

FOREIGN PATENT DOCUMENTS

| | | |
|---|---|---|
| EP | 0 127 483 B1 | 10/1989 |
| EP | 0 164 740 B1 | 4/1990 |
| EP | 0 432 755 B1 | 5/1995 |
| EP | 0 432 763 B1 | 5/1995 |
| EP | 0 685 586 A2 | 12/1995 |
| EP | 0 687 757 A2 | 12/1995 |
| EP | 0 452 727 B1 | 3/1996 |
| EP | 0 758 543 A1 | 2/1997 |
| EP | 0 713 546 B1 | 3/1997 |
| EP | 0 677 284 B1 | 6/1999 |
| EP | 0 919 212 A2 | 6/1999 |
| EP | 0 945 251 A1 | 9/1999 |
| EP | 0 945 536 A2 | 9/1999 |
| EP | 0 955 159 A1 | 11/1999 |
| EP | 0 823 878 B1 | 8/2000 |
| JP | 08299385 A | 11/1996 |
| WO | WO 94/19179 A1 | 9/1994 |
| WO | WO 96/10979 A1 | 4/1996 |
| WO | WO 96/10979 * | 4/1996 |
| WO | WO 97/11662 A1 | 4/1997 |
| WO | WO 97/47264 | 12/1997 |
| WO | WO 99/37476 A1 | 7/1999 |
| WO | WO 99/55273 A1 | 11/1999 |
| WO | WO 99/55532 A1 | 11/1999 |
| WO | WO 99/67081 | 12/1999 |
| WO | WO 00/76430 A1 | 12/2000 |
| WO | WO 01/45616 A1 | 6/2001 |

* cited by examiner

LAMINATE WEB

FIELD OF THE INVENTION

This invention relates to a multilayer laminate web, and more particularly to a laminate web wherein at least a central layer is apertured. In some embodiments the entire multilayer laminate web is apertured.

BACKGROUND OF THE INVENTION

Laminate webs formed by the joining of discrete webs in a layered relationship are well known in the art. For example, often laminate nonwoven webs are utilized in disposable absorbent articles such as diapers and adult incontinence products. Such laminated webs can be used as a topsheet, backsheet, or side panels. One example of a laminate web is a film/nonwoven laminate useful for a stretch side panel of a disposable diaper. Nonwoven/nonwoven laminates are also utilized to provide additional bulk or softness to a web component. Likewise, film/film laminate webs can provide benefits by combining the characteristics of various films in a layered relationship. Laminate webs can also be called composite webs.

Less common examples of laminate webs include laminates of dissimilar materials. The materials may be dissimilar in mechanical tensile properties, thermal properties, or visual/tactile properties. For example, a nonwoven web may be joined to a relatively stiff fabric to provide for a soft surface feel to the fabric. The dissimilar materials may be joined by melt bonding, adhesive bonding, ultrasonic bonding, and the like. Bonding methods are often determined by the materials themselves, but often require adhesive bonding. For example, a laminate or composite of materials having widely differing melt properties may require an adhesive layer between laminate layers. Even materials having similar melt properties, such as nonwoven and thermoplastic film materials are often joined by adhesive for adequate bonding to prevent unwanted delamination. Such processing methods can be expensive due to the addition of adhesive, and the resulting laminate is often relatively stiff, depending on the level of adhesive added.

Apertured laminate webs can be made by methods in the art. One beneficial method of aperturing a nonwoven web, for example, is disclosed in commonly-assigned U.S. Pat. No. 5,916,661, issued to Benson et al. on Jun. 29, 1999, which is hereby incorporated herein by reference. Benson '661 teaches a laminate material having, for example, at least one layer of a spunbonded web joined to at least one layer of a meltblown web, a bonded carded web, or other suitable material. Such apertured webs are useful as the topsheet in a disposable absorbent article. However, Benson '661 does not teach apertured laminate webs comprising completely dissimilar materials (e.g., materials of different material classes or having differing material properties).

As mentioned, nonwoven webs are beneficial as components of disposable absorbent articles, such as diapers, incontinence briefs, training pants, feminine hygiene garments, and the like, as well as in wipes such as disposable wet wipes. Nonwovens are also beneficial components of other disposable garments, durable garments, automotive components, upholstered furniture, filtration media, and other consumer or commercial goods. Nonwovens used in these and other applications benefit from their wide range of visual and tactile properties. However, used alone, such nonwovens are limited in the range of beneficial properties, including visual, tactile, strength or absorbent properties due to the limits of known methods of making, particularly as compared to woven or knitted materials.

Accordingly, it would desirable to have a laminate web having component webs of different material properties.

Additionally, it would be desirable to have a laminate web formed by joining the constituent layers without adhesive.

Further, it would be desirable to have an apertured laminate web having visually distinct regions giving a fabric-like or knit-like look and feel.

BRIEF SUMMARY OF THE INVENTION

A laminate web is disclose, the laminate web comprising a first web, a second web joined to the first web at a plurality of discrete bond sites; and a third material disposed between at least a portion of the first and second nonwovens. The third material is apertured in regions adjacent the bond sites, such that the first and second nonwoven webs are joined through the apertures.

In one embodiment an apertured laminate web is disclosed, having a first extensible web having a first elongation to break, and a second extensible web joined to the first extensible web at a plurality of bond sites, the second extensible web having a second elongation to break A third web material is disposed between the first and second nonwovens, the third web material having a third elongation to break which is less than both of the first or second elongations to break.

In a further embodiment, an apertured laminate web is disclose, having first and second extensible webs being joined at a plurality of discrete bond sites and a third material disposed between the first and second nonwoven webs. The first and second nonwoven webs are in fluid communication via the apertures and have distinct regions being differentiated by at least one property selected from the group consisting of basis weight, fiber orientation, thickness, and density.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Figure 1:
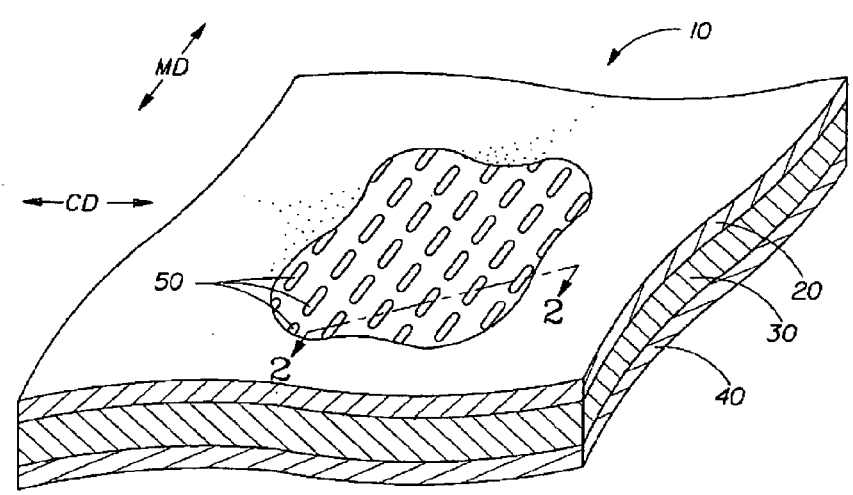
FIG. 1 is a perspective of one embodiment of a laminate web of the present invention.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

As used herein, the term "nonwoven web", refers to a web that has a structure of individual fibers or threads which are interlaid, but not in any regular, repeating manner. Nonwoven webs have been, in the past, formed by a variety of processes, such as, for example, meltblowing processes, spunbonding processes and bonded carded web processes.

As used herein, the term "microfibers", refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fibers", refers to small diameter fibers which are formed by extruding a molten thermoplastic material as filaments from a plurality of fine, usually circular, capillaries of a spinneret with the diameter of the extruded filaments then being rapidly reduced by drawing.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiaotactic and random symmetries.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force.

As used herein, the term "nonelastic" refers to any material which does not fall within the definition of "elastic" above.

As used herein, the term "extensible" refers to any material which, upon application of a biasing force, is elongatable, at least about 50 percent without experiencing catastrophic failure.

The Laminate Web

The laminate web 10 of the present invention comprises at least three layers or plies, disposed in a layered, face-to-face relationship, as shown in FIG. 1. The layers should be sufficiently thin to be processable as described herein, but no actual thickness (i.e., caliper) is considered limiting. A first outer layer 20, is preferably a nonwoven web having a predetermined extensibility and elongation to break. A second outer layer, 40, is preferably the same material as first outer layer 20, but may be a different material, also having a predetermined extensibility and elongation to break. At least one third central layer 30 is disposed between the two outer layers. The laminate web 10 is processed by thermal calendaring as described below to provide a plurality of melt bond sites 50 that serve to couple the outer layers 20 and 40, thereby forming the constituent layers into a unitary web. While the laminate web 10 is disclosed primarily in the context of nonwoven webs and composites, in principle the laminate web 10 can be made out of any web materials that meet the requirements, (e.g., melt properties, extensibility) as disclosed herein. For example, the constituent layers can be films, micro-porous films, apertured films, and the like.

One of the unexpected advantages of the present invention is the discovery that novel web properties can be exhibited by the choice of central layer 30 disposed between the two outer layers. In one embodiment, as shown in cross-section in FIG. 2, central layer 30 can be apertured, without aperturing the two outer layers to provide a three-layer laminate characterized by the laminate web 10 being un-apertured, while the central layer 30 is apertured. The laminate web 10 is further characterized in that the joining of the three plies into a coherent web is achieved in the absence of adhesive. That is, no adhesive is used to bond the plies together; joining is achieved by the thermal melt bonding of the two outer layers together at the melt bond sites 50.

Figure 2:
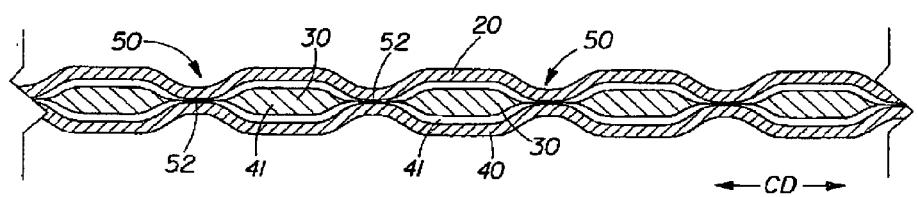
FIG. 2 is a cross-sectional view of a portion of the laminate web shown in FIG. 1.

As shown in FIG. 2, central layer 30 is chosen such that when the constituent web layers of laminate web 10 are processed as detailed below, portions of central layer 30 in the region of the melt bond sites 50 separate to permit the first layer 20 to melt bond directly to the second outer layer 40 at the interface of the two materials 52 at melt bond sites 50. Without being bound by theory, it is believed that the process of the present invention facilitates such separation of central layer 30 by shearing, cutting, or otherwise fracturing the central layer, and displacing the material of the central layer sufficiently to permit thermal bonding of the two outer layers. Thus, central layer 30 should be chosen to have properties that permit such cutting through, such as relatively low extensibility, relatively high frangibility, or relatively high deformability, such that the material of central layer 30 can be "squeezed" out of the region of thermal bond sites 50.

Figure 3:
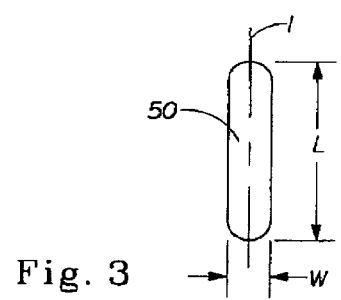
FIG. 3 is a magnified detail view of one bond site of a laminate web of the present invention.

Without being bound by theory, it is believed that to accomplish the displacement of central layer 30 to form apertures therein and to bond the outer layers, the thermal point calendaring described below should form thermal bond sites having a narrow width W dimension and a high aspect ratio. For example, FIG. 3 shows the melt area of a single melt bond site 50 having a narrow width dimension W and a high aspect ratio, i.e., the length, L, is much greater than the width, W. The length L should be selected to permit adequate bond area while width W is sufficiently narrow such that the protuberance used to form the bond site (as described below) can cut, shear, or otherwise pierce the central layer 30 at the region of the bond sites by the method described below. Width W can be between about 0.003 inches and 0.020 inches, but in a preferred embodiment, is between about 0.005 inches and 0.010 inches, and may be adjusted depending on the properties of central layer 30.

It is believed that the aspect ratio of can be as low as about 3 (i.e., ratio of L/W equals 3/1). It can also be between about 4 and 20. In one preferred embodiment, the aspect ratio was about 10. The aspect ratio of the melt bond sites 50 is limited only by the corresponding aspect ratio of the point bonding protuberances of the calendaring roller(s), as detailed below.

In a preferred embodiment, the longitudinal axis of each bond site, 1, which corresponds directionally to the length dimension of bond site 50, is disposed in a regular, repeating pattern oriented generally in the machine direction, MD as shown in FIG. 1. But the bond sites may be disposed in a regular, repeating pattern oriented in the cross machine direction, or randomly oriented in a mixture of cross and machine directions. For example, the bond sites 50 can be disposed in a "herringbone" pattern.

The resulting web of the present invention, as shown in cross-section in FIG. 2, is a laminate web 10 that is itself unapertured, but the central layer 30 is apertured adjacent the regions of the bond sites 50. By "unapertured" is meant that, on the whole, the laminate web 10 is considered unapertured. It is recognized that the un-apertured laminate web 10 of the present invention may have localized cut through, or tearing at bond sites 50 due to materials and processing variability or post lamination handling. Ideally, such cut through of the entire web is minimized and eliminated. Likewise, it is recognized that in some instances, there may not be complete cut through of the central layer 30 at all locations of bond sites 50 such that some localized portions of central layer 30 may not be apertured (and the outer layers not bonded). Nevertheless, the description herein is made for the laminate web 50 as a whole, and is not meant to be limited by aberrations or anomalies due to potential material or processing variables.

The central layer 30 itself need not be thermally compatible with the outer layers. The central layer 30 need not even be melt processible. It can be, for example, a cellulosic material, such as paper; a metallic material, such as a metal foil; a woven or knit material, such as cotton or rayon blends; or a thermoset material, such as a polyester or aromatic polyamide film. The central layer 30 can be another nonwoven having suitable properties for processing into an apertured layer. If central layer 30 has a melting point, it is preferably at least about 20 degrees Centigrade higher than the outer layers. However, central layer 30 need not have a melting point, and may simply experience softening at the calendaring temperatures required to bond the laminate. In certain central layer materials, such as metal foils, there is not even any softening due to thermal processing of the web.

The wide range of possible central layer materials permits a surprising variety of structures of the present invention, each having beneficial application in a wide assortment of end uses. For example, when outer layers of nonwoven material are used with a central layer of metal foil, the resulting laminate is a flexible, soft, formable, metallic web that is relatively silent when folded, crumpled or otherwise deformed. Such a material can be used in applications requiring electrical shielding, for example. When a central layer of tissue paper is used, the resulting laminate is a soft, bulky, absorbent web. Such a laminate is suitable for use as a wiping implement, for example. Further, since the laminate web 10 is formed without the use of thermoplastic adhesives, durable, garment-like properties can be obtained. Such laminates can be laundered a number of times before suffering unacceptable wear.

Another benefit of the present invention is obtained when the thermally bonded laminate web described above is stretched or extended in a direction generally orthogonal to the longitudinal axis, 1, of melt bond sites 50. The melt bonding at the melt bond sites 50 tends to make localized weakened portions of the web at the bond sites. Thus, as portions of the web 10 are extended in a direction generally orthogonal to the longitudinal axis 1 of bond sites 50, the material at the bond site fails in tension and an aperture is formed. The relatively high aspect ratio of melt bond sites 50, permits a relatively large aperture to be formed upon sufficient extension. When the laminate web 10 is uniformly tensioned, the result is a regular pattern of a plurality of apertures 60 corresponding to the pattern of melt bond sites 50.

Figure 4:
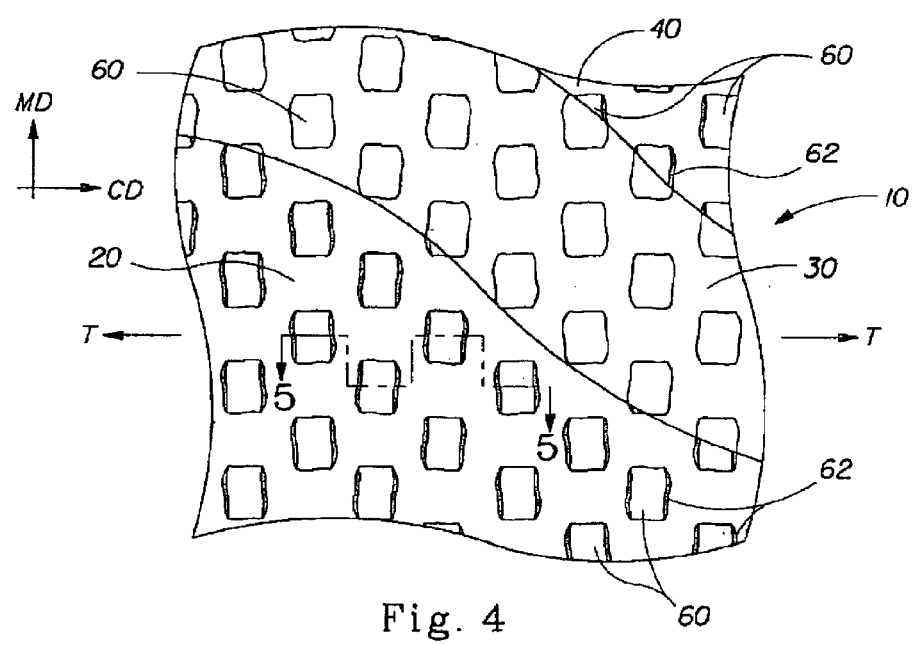
FIG. 4 is a top plan view of another embodiment of the laminate web of the present invention.

FIG. 4 shows a partially cut-away representation of an apertured laminate of the present invention. As shown, the partial cut-away permits each layer or ply to be viewed in a plan view. The laminate web 10 shown in FIG. 4 is produced after the thermally bonded laminate is stretched in a direction orthogonal to the longitudinal axis of the melt bond sites, in this case, in the cross-machine direction, CD. As shown, where formerly were melt bond sites 50, apertures 60 are produced as the relatively weak bond sites fail in tension. Also as shown, central layer 30 can remain generally uniformly distributed within laminate 10, depending on the material properties of central layer 30. For example, if central layer 30 is more extensible than outer layers 20 or 40, then it simply extends, possibly by plastic deformation, but remains generally uniformly distributed in the unapertured regions of web 10. For example, if a thermoplastic film is utilized as the central layer 30, it extends, either extensibly or elastically (depending on the type of film), but can remain generally uniform, for example, in density or basis weight.

When apertures 60 are formed, the thermally bonded portions of outer layers 20 and 40 remain primarily on the portions of the aperture perimeters corresponding to the length dimension of bond sites 50. Therefore, each aperture 60 does not have a perimeter of thermally bonded material, but only portions remain bonded, represented as 62 in FIG. 4. One beneficial property of such a laminate web is that once apertured, fluid communication with the central layer is facilitated. Thus, an absorbent central layer 30 can be used between two relatively non-absorbent outer layers, and the laminate 10 could be an absorptive wiper with a relatively dry to the touch outer surface.

Figure 5:
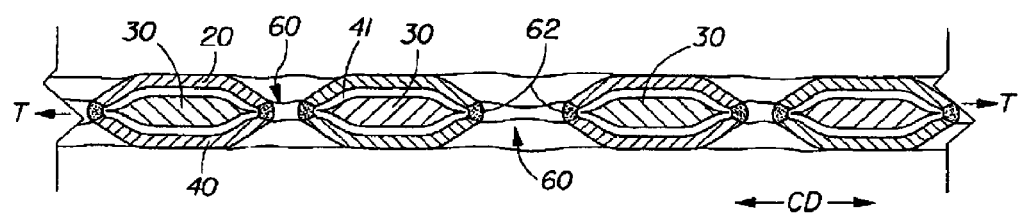
FIG. 5 is a cross-sectional view of a portion of the laminate web shown in FIG. 4.

FIG. 5 is a schematic representation of the cross-section denoted in FIG. 4. As shown, apertures 60 form when the laminate web is elongated in the direction T.

Another benefit of the present invention is obtained when the laminate is extended as described with reference to FIG. 4, but the central layer 30 is chosen to have an elongation to break less than either of the two outer layers, that is, it fails in tension at a lower extensibility than does either of the outer layers. Thus, when the laminate is extended generally orthogonal to the longitudinal axis, 1, of melt bond sites 50, outer layers 20 and 40 extend to form apertures. However, central layer 30, which has an elongation to break less than that of the outer layers, fractures upon sufficient extension, such that after extension central layer 30 is no longer uniformly distributed over the non-apertured regions of the laminate web 10.

An example of one embodiment of a web having a central layer having an elongation to break less than either of the two outer layers is shown partially cut-away in FIG. 5. The partial cut-away permits each layer or ply to be viewed in a plan view. As shown, after extension, central layer 30 becomes fragmented, forming discontinuous regions of the central layer material. These discontinuous regions may be relatively uniformly distributed, such as in rows as shown in FIG. 5, or may be relatively randomly distributed, depending on the pattern of melt bond sites 50 and the method of extension employed. One example of a web 10 having a structure similar to that shown in FIG. 5 is a web having outer layers of relatively extensible nonwovens, with a central layer of relatively low extensibility tissue paper.

Figure 6:
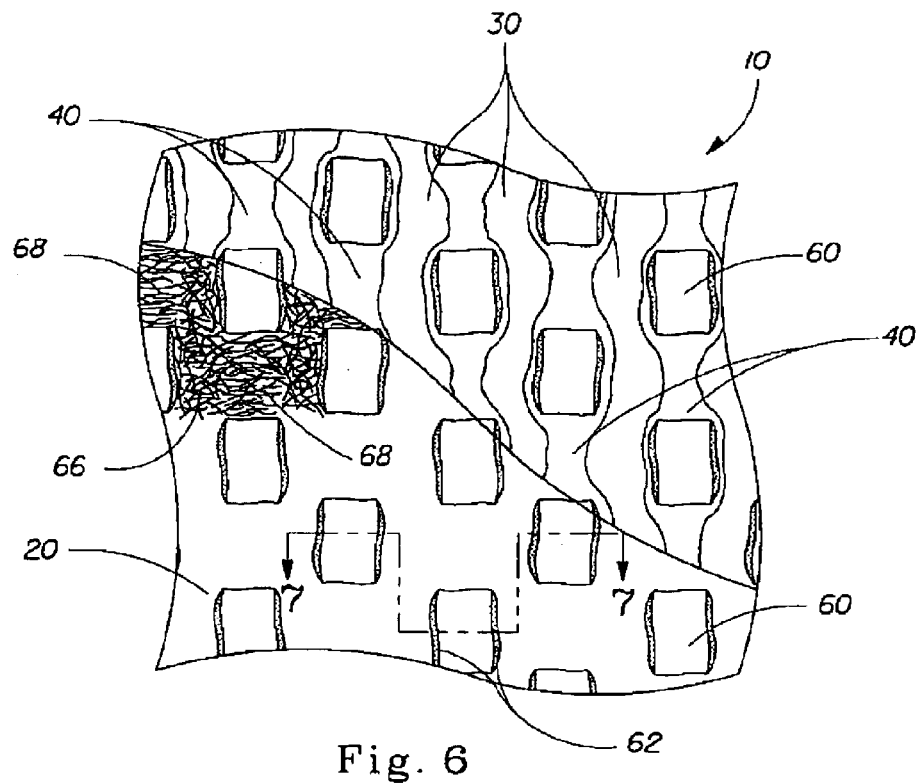
FIG. 6 is a top plan view of another embodiment of the laminate web of the present invention.

One surprising beneficial characteristic of the laminate web structure of the present invention described with reference to FIG. 6 is the presence of distinct regions in the non-apertured portion of the web being differentiated by at least one property selected from the group consisting of basis weight, thickness, or density. As shown in the cross-section of FIG. 7, several such regions can be differentiated. In a preferred embodiment, the regions are visually distinct, giving the laminate an aesthetically pleasing look and feel. The regions may also give the laminate a garment-like or knit-like texture and hand.

Figure 7:
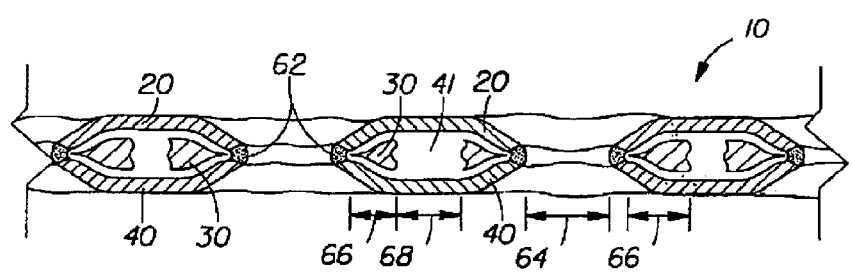
FIG. 7 is a cross-sectional view of a portion of the laminate web shown in FIG. 6.

With reference to FIG. 7, several structurally distinct regions can be identified in the cross-section shown. The region denoted 64 corresponds to the aperture 60. In the non-apertured area of the web, a region 66 is a relatively high basis weight region comprising central layer 30. Region 68 represents the portion of the laminate web in which central layer 30 has fractured and separated, i.e., is no longer fully present, forming a relatively low basis weight region of web 10. In general, the higher basis weight regions will also be correspondingly higher density regions, but need not be so. For example, a post-extension embossing process can be applied to web 10 to form regions of multiple densities in addition to the regions of multiple basis weight. For either the high basis weight regions or the high density regions, often the differences can be discernible by simply rubbing between the fingers.

In general, for a laminate web 10 having generally parallel rows of melt bond sites 50 extending in the machine direction MD, which correspondingly form generally parallel rows of apertures when extended, and having a central layer with a lower elongation to break than the outer layers, the resulting extended, apertured laminate web 10 is characterized by generally low basis weight, low density regions between the apertures in the machine direction, MD, e.g., region 68 in FIGS. 6 and 7. Likewise, the laminate web 10 is characterized by relatively high basis weight, high density regions between adjacent rows of apertures in the cross-machine direction, CD, e.g., region 66 in FIG. 7. By choice of central layer material 30 and possibly post laminating operations, e.g., an embossing process, the thickness of the laminate web can likewise be varied, the thicker regions generally corresponding to the higher density regions.

Another embodiment of a laminate web of the present invention utilizing nonwoven webs as the outer layers is characterized by distinct regions differentiated by fiber orientation. Differential fiber orientation can be achieved by providing for localized regions within the web that experience greater extension than other regions. For example, by locally straining the web 10 to a greater degree in the regions corresponding to regions 68 in FIG. 6, regions of significant fiber reorientation are formed. Such localized straining is possible by the method of the present invention detailed below.

Figure 8:
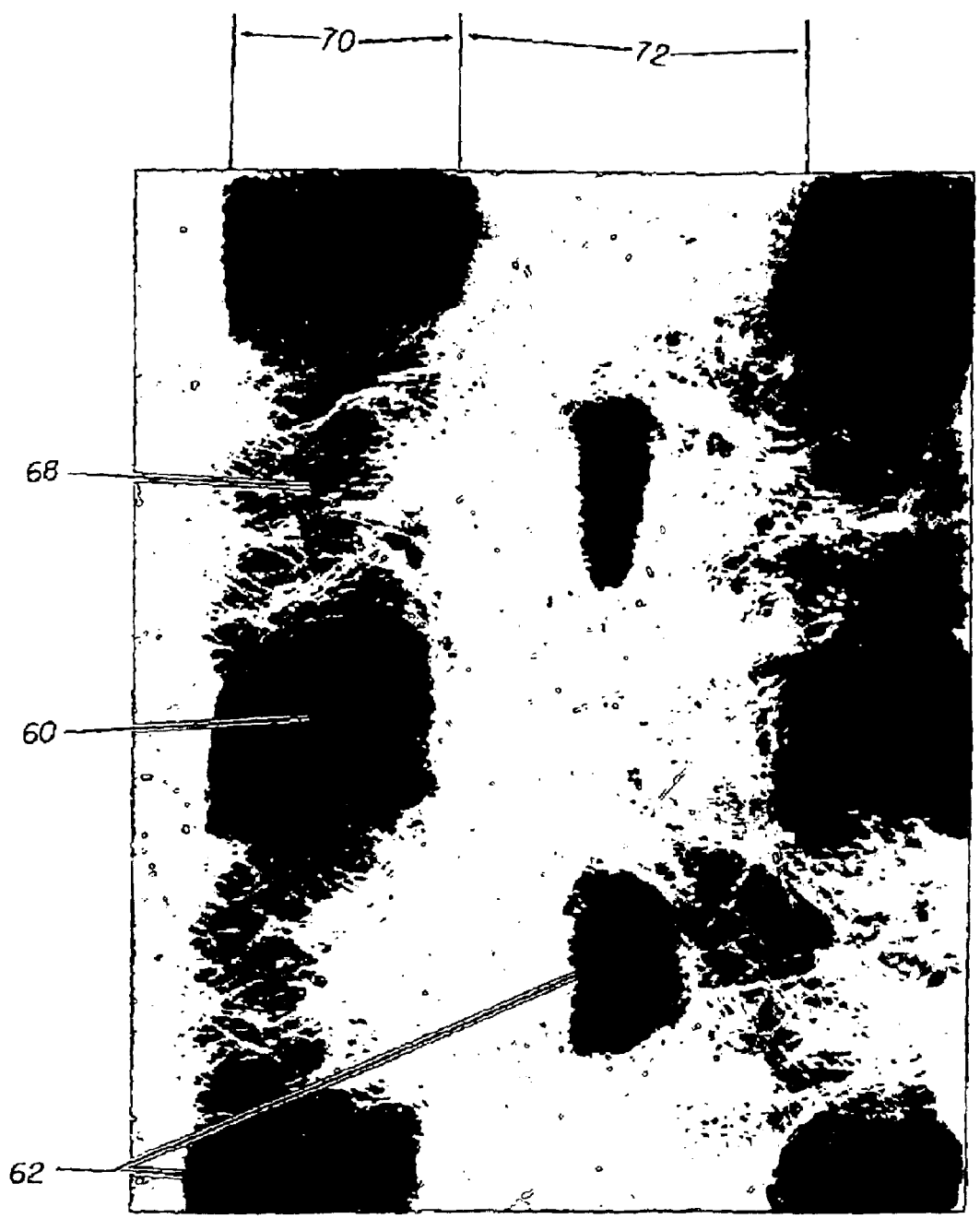
FIG. 8 is a photomicrograph of one embodiment of a laminate web of the present invention.

FIG. 8 is a photomicrograph showing in magnified detail a web of the present invention which has been extended to form apertures, and locally extended to produce regions 68 of fiber reorientation. As can be seen in FIG. 8, by locally extending portions of the web to a greater extent than others, the apertures formed thereby can be of different sizes. Thus, the region denoted generally as 70 in FIG. 8 has undergone more strain (i.e., local extension) than the region denoted by 72. Thus, the apertures in region 70 are larger than those in region 72, and the basis weight of the nonwoven web material in region 72 is less than the basis weight of the nonwoven web in region 70. In addition to the difference in basis weight due to localized strain differentials, the laminate web of the present invention can also exhibit distinct regions 68 of fiber reorientation. In these regions, the fibers have been reoriented from a generally random orientation to a predominant orientation in the direction of extension.

To make a web 10 as shown in FIG. 6, central layer 30 can be any of a great number of dissimilar materials. For example, if outer layers 20 and 40 are nonwoven webs having a relatively high elongation to break, central layer 30 can be paper, tissue paper, thermoplastic film, metal foil, closed or open cell foam, or any other material that has a relatively low elongation to break compared to the two outer layers. The outer layer materials may themselves be dissimilar, with the only constraint being that the central layer be relatively less extensible in the direction of extension to form apertures.

Additionally, more than one central layer 30 can be used with beneficial results. For example, a structure comprising a cellulosic tissue central web and a polymeric film central web between two nonwoven webs can produce an absorptive wiping article with one side being relatively more absorptive than the other. If the film layer is a three-dimensional formed film, the film side can provide added texture to the laminate which is beneficial in many wiping applications. Macroscopically-expanded, three-dimensional formed films suitable for use in the present invention include those described in commonly-assigned U.S. Pat. No. 3,929, 135 issued to Thompson on Dec. 30, 1975, and U.S. Pat. No.

4,342,314 issued to Radel et al. on Aug. 3, 1982, both patents hereby incorporated herein by reference.

The (or "a") central layer can also be elastomeric, and can be an elastomeric macroscopically-expanded, vacuum-formed, three-dimensional formed film, such as described in commonly-assigned U.S. Ser. No. 08/816,106, entitled "Tear Resistant Porous Extensible Web" filed by Curro et al. on Mar. 14, 1997, and hereby incorporated herein by reference. Further, the (or "a") central layer can be a three-dimensional formed film having micro-apertures such as described in commonly-assigned U.S. Pat. No. 4,629,643 issued to Curro et al. on Dec. 16, 1986, and U.S. Pat. No. 4,609,518, issued to Curro et al. on Sep. 2, 1986, both of which are hereby incorporated herein by reference.

The (or "a") central layer can be a web material having a strainable network as disclosed in U.S. Pat. No. 5,518,801 issued to Chappell et al. on May 21, 1996, and hereby incorporated herein by reference. Such a web can be a structural elastic-like film (SELF) web, formed by, for example, embossing by mating plates or rolls.

The (or "a") central layer can be an absorbent open cell foam web material. Particularly suitable absorbent foams for high performance absorbent articles such as diapers have been made from High Internal Phase Emulsions (hereafter referred to as "HIPE"). See, for example, U.S. Pat. No. 5,260,345 (DesMarais et al), issued Nov. 9, 1993 and U.S. Pat. No. 5,268,224 (DesMarais et al), issued Dec. 7, 1993, hereby incorporated herein by reference. These absorbent HIPE foams provide desirable fluid handling properties, including: (a) relatively good wicking and fluid distribution characteristics to transport the imbibed urine or other body fluid away from the initial impingement zone and into other regions of the foam structure to allow for subsequent gushes of fluid to be accommodated; and (b) a relatively high storage capacity with a relatively high fluid capacity under load, i.e. under compressive forces.

The central layer 30 may comprise absorbent gelling materials. For example, supersorbers or hydrogel materials may provide for superior absorbency when the laminate web of the present invention is used as an absorbent wipe or a core in a disposable absorbent article. By "hydrogel" as used herein is meant an inorganic or organic compound capable of absorbing aqueous fluids and retaining them under moderate pressures. For good results the hydrogels should be water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl pyridine and the like.

One benefit of the laminate of the present invention is the ability to make a laminate structure of dissimilar materials without the use of adhesive for joining. Because the central layer of the laminate web 10 is penetrated by the protuberances of the calendaring roll at melt bond sites, it can comprise non-thermally-bondable materials. The plurality of melt bond sites 50 are sufficient to keep the component webs together in the laminate web, so that the laminate web behaves as a unitary web for processing integrity and use, without unwanted delamination. However, in some embodiments, and for certain materials, it may be beneficial to apply adhesive between at least two of the constituent layers.

The laminate web of the present invention, being bonded by a plurality of relatively closely spaced thermal bond sites (without the use of thermoplastic adhesives) can be beneficially used for durable articles. For example, the laminate web of the present invention, having a clothlike feel and appearance, can be used in durable garments. Certain embodiments of the laminate web of the present invention can survive repeated washing and drying in household washing and drying equipment, depending on the component webs of the laminate, and the level of thermal bonding. Due to the knit-like or fabric-like look and feel of certain embodiments of the present invention, such durability can result in durable garment components such as interliners and the like.

Method of Making

Figure 9:
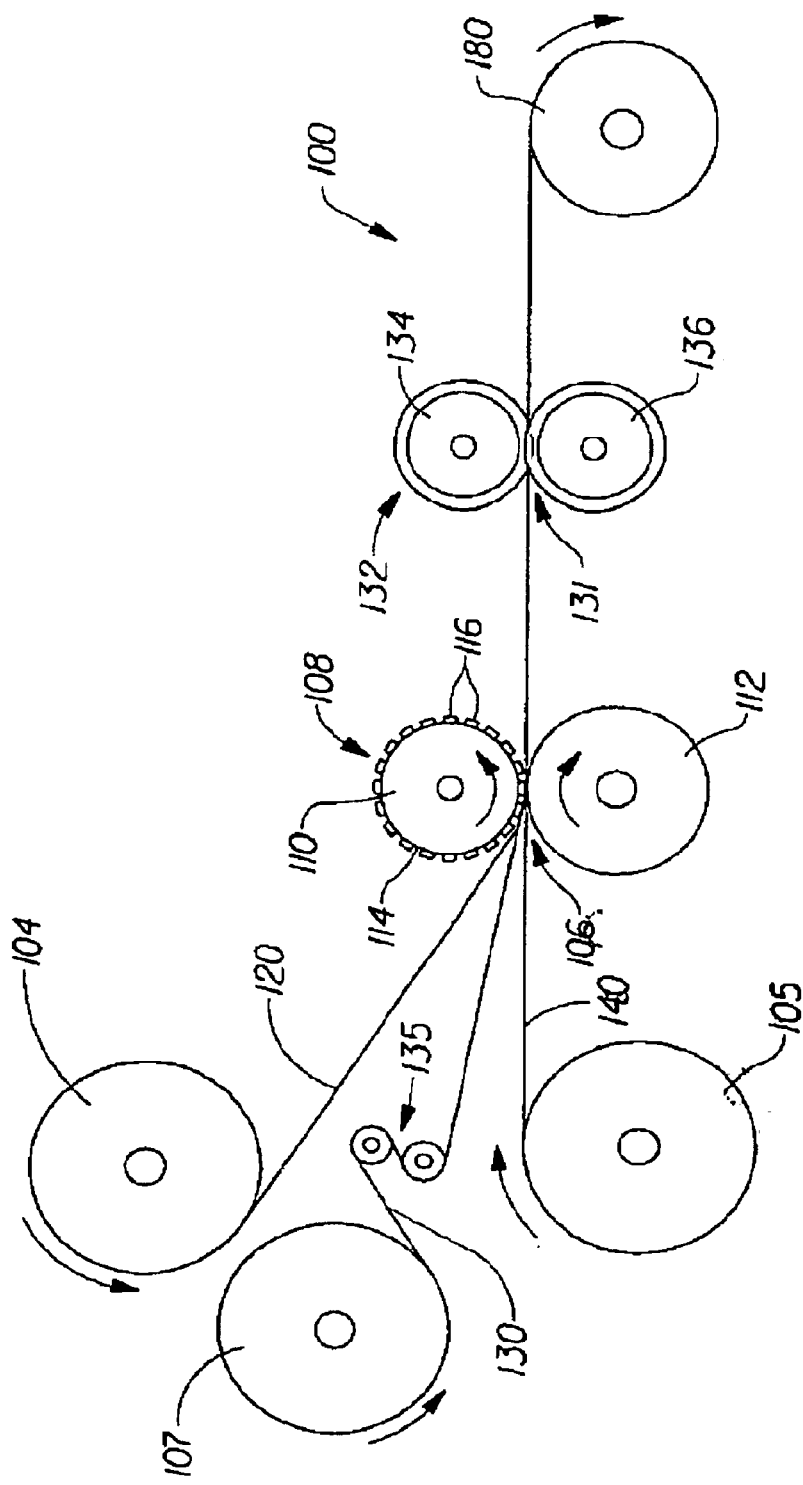
FIG. 9 is a schematic representation of a process for making a laminate web of the present invention.

Referring to FIG. 9 there is schematically illustrated at 100 a process making a laminate web of the present invention.

A first relatively extensible web 120 is unwound from a supply roll 104 and travels in a direction indicated by the arrows associated therewith as the supply roll 104 rotates in the direction indicated by the arrows associated therewith. Likewise a second relatively extensible web 140 is unwound from supply roll 105. A central layer 130 is likewise drawn from supply roll 107. The three components (or more, if more than one central layer is used) pass through a nip 106 of the thermal point bond roller arrangement 108 formed by rollers 110 and 112.

Either outer layer can comprise a formed film, such as a three-dimensional formed film having micro-apertures such as described in commonly-assigned U.S. Pat. No. 4,629,643 issued to Curro et al. on Dec. 16, 1986, and U.S. Pat. No. 4,609,518, issued to Curro et al. on Sep. 2, 1986, both of which are hereby incorporated herein by reference.

In a preferred embodiment, both outer layers comprise nonwoven materials, and may be the identical. The nonwoven material may be formed by known nonwoven extrusion processes, such as, for example, known meltblowing processes or known spunbonding processes, and passed directly through the nip 106 without first being bonded and/or stored on a supply roll. However, in a preferred embodiment, the nonwoven webs are themselves thermally point bonded (consolidated) webs commercially available on supply rolls.

The nonwoven web outer layer(s) may be elastic or nonelastic. The nonwoven web may be any melt-fusible web, including a spunbonded web, a meltblown web, or a bonded carded web. If the nonwoven web is a web of meltblown fibers, it may include meltblown microfibers. The nonwoven web may be made of fiber forming polymers such as, for example, polyolefins. Exemplary polyolefins include one or more of polypropylene, polyethylene, ethylene copolymers, propylene copolymers, and butene copolymers. The nonwoven web can have a basis weight between about 10 to about 60 grams per square meter (gsm), and more preferably about 15 to about 30 gsm.

The nonwoven web outer layers may themselves be a multilayer material having, for example, at least one layer of a spunbonded web joined to at least one layer of a meltblown web, a bonded carded web, or other suitable material. For example, the nonwoven web may be a multilayer web having a first layer of spunbonded polypropylene having a basis weight from about 0.2 to about 8 ounces per square yard, a layer of meltblown polypropylene having a basis weight from about 0.2 to about 4 ounces per square yard, and a second layer of spunbonded polypropylene having a basis weight from about 0.2 to about 8 ounces per square yard. Alternatively, the nonwoven web may be a single layer of material, such as, for example, a spunbonded web having a basis weight from about 0.2 to about 10 ounces per square yard or a meltblown web having a basis weight from about 0.2 to about 8 ounces per square yard.

The nonwoven web outer layers may also be a composite made up of a mixture of two or more different fibers or a mixture of fibers and particles. Such mixtures may be formed by adding fibers and/or particulates to the gas stream in which the meltblown fibers or spunbond fibers are carried so that an intimate entangled co-mingling of fibers and other materials, e.g., wood pulp, staple fibers and particles occurs prior to collection of the fibers.

Prior to processing by the method of the present invention, the nonwoven web outer cover of fibers can be (but need not be, e.g., tow fibers can be used) joined by bonding to form a coherent web structure. Suitable bonding techniques include, but are not limited to, chemical bonding, thermobonding, such as point calendering, hydroentangling, and needling.

Figure 10:
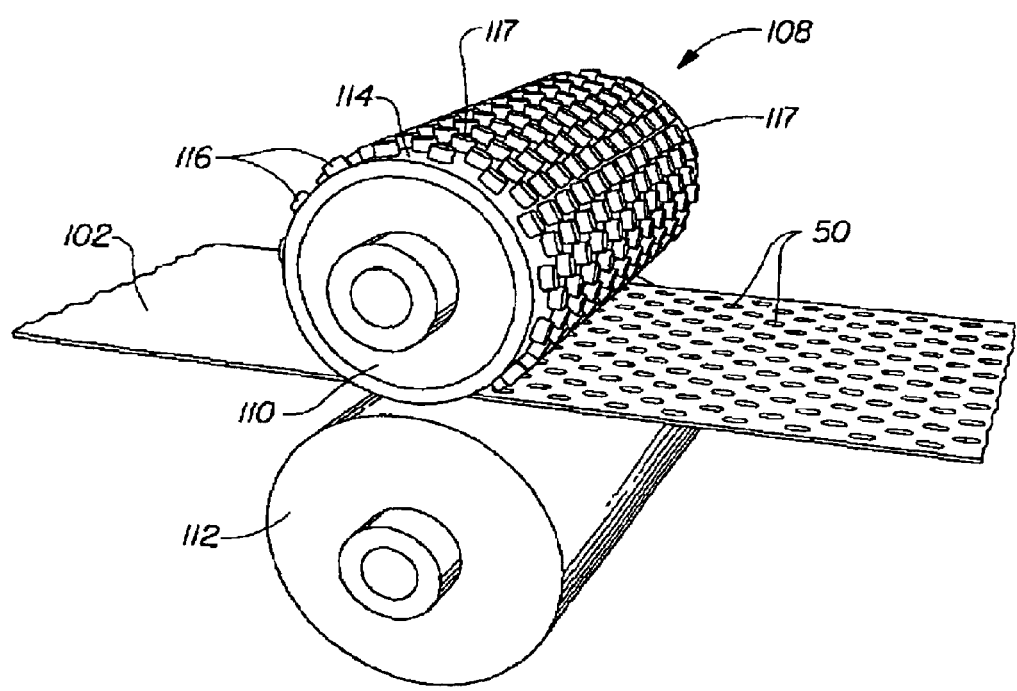
FIG. 10 is a perspective view of a melt bond calendaring apparatus.

Referring to FIGS. 9 and 10, the nonwoven thermal bond roller arrangement 1108 preferably comprises a patterned calendar roller 110 and a smooth anvil roller 112. One or both of the patterned calendar roller 110 and the smooth anvil roller 112 may be heated and the pressure between the two rollers may be adjusted by well known means to provide the desired temperature, if any, and pressure to concurrently displace central layer 30 at melt bond sites, and melt bond the two outer layers together at a plurality of bond sites.

Figure 11:
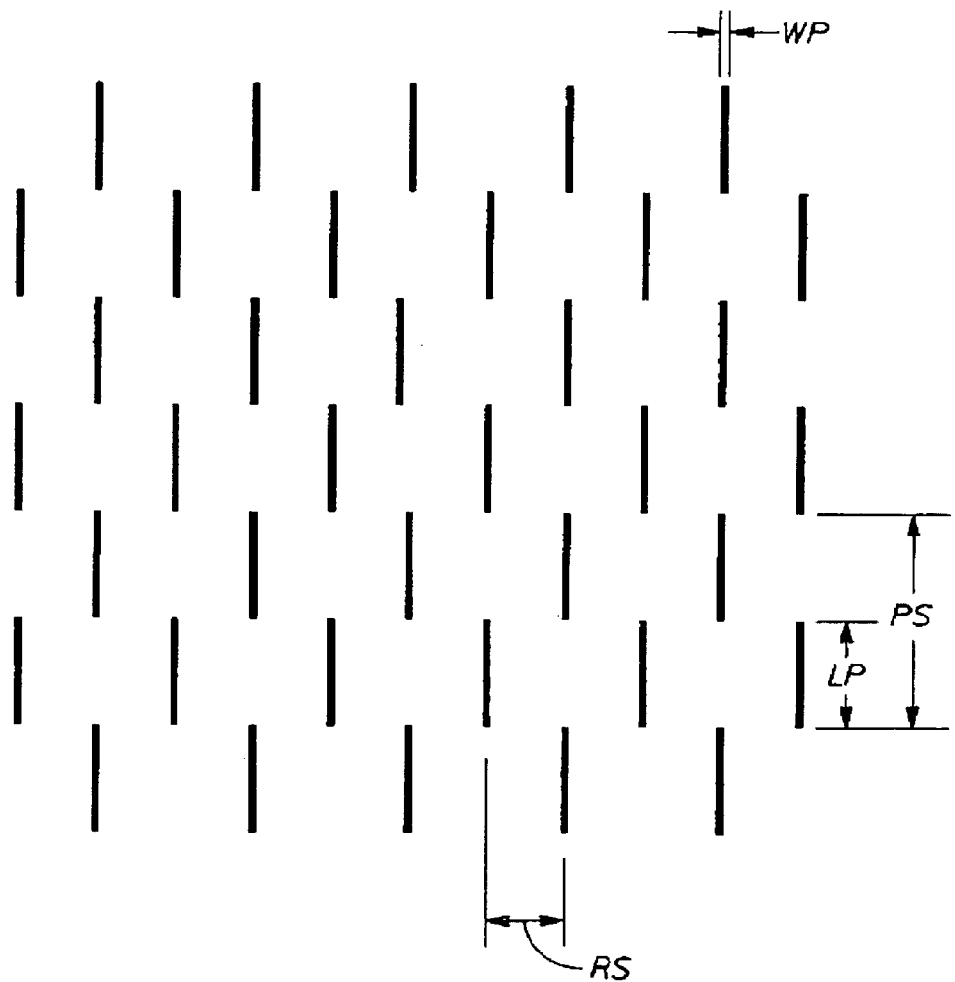
FIG. 11 is a schematic representation of a pattern for the protuberances of the calendaring roll.

The patterned calendar roller 110 is configured to have a circular cylindrical surface 114, and a plurality of protuberances or pattern elements 116 which extend outwardly from surface 114. The protuberances 116 are disposed in a predetermined pattern with each protuberance 116 being configured and disposed to displace central layer 30 at melt bond sites, and melt bond the two outer layers together at a plurality of locations. One pattern of protuberances is shown in FIG. 11. As shown, the protuberances 116 have a relatively small width, WP, which can be between about 0.003 inches and 0.020 inches, but in a preferred embodiment is about 0.010 inches. Protuberances can have a length, LP, of between about 0.030 inches and about 0.200 inches, and in a preferred embodiment has a length of about 0.100 inches. In a preferred embodiment, the protuberances have an aspect ratio of 10. The pattern shown is a regular repeating pattern of staggered protuberances, generally in rows, each separated by a row spacing, RS, of about between about 0.010 inches and about 0.200 inches. In a preferred embodiment, row spacing RS is about 0.060 inches. The protuberances can be spaced apart within a row by a protuberance spacing, PS generally equal to the protuberance length, LP. But the spacing and pattern can be varied in any way depending on the end product desired.

As shown in FIG. 10, patterned calendar roller 110 can have a repeating pattern of protuberances 116 which extend about the entire circumference of surface 114. Alternatively, the protuberances 116 may extend around a portion, or portions of the circumference of surface 114. Likewise, the protuberances 116 may be in a non-repeating pattern, or in a repeating pattern of randomly oriented protuberances.

The protuberances 116 are preferably truncated conical shapes which extend radially outwardly from surface 114 and which have rectangular or somewhat elliptical distal end surfaces 117. Although it is not intended to thereby limit the scope of the present invention to protuberances of only this configuration, it is currently believed that the high aspect ratio of the melt bond site 50 is only achievable if the protuberances likewise have a narrow width and a high aspect ratio at the distal end surfaces 117, as shown above with reference to FIG. 11. Without being bound by theory, it is believed that other suitable shapes for distal ends 117 may include, but are not limited to circular, square, rectangular, etc., if they facilitate the bonding and aperturing of the present invention. The roller 110 is preferably finished so that all of the end surfaces 117 lie in an imaginary right circular cylinder which is coaxial with respect to the axis of rotation of roller 110.

The height of the protuberances should be selected according to the thickness of the laminate being bonded. In general, the height dimension should be greater than the maximum thickness of the laminate web during the calendaring process, so that adequate bonding occurs at the bond sites, and only at the bond sites.

Anvil roller 112, is preferably a smooth surfaced, right circular cylinder of steel.

After passing through nip 106, the three (or more) component webs 120, 130, and 140, shown together as web 102 in FIG. 10, have been formed into laminate web 10. At this point in the process, the outer layers are thermally bonded and unapertured, as shown in FIGS. 1 and 2. Central layers(s) 30, from web 130, is apertured, having been displaced by protuberances 116 in nip 106.

The laminate web 10 may be further processed to form apertures in the hole laminate web extending portions of the web in a direction orthogonal to the axis 1 of bond sites 50. As shown in FIGS. 9 and 10, the axis 1 is generally parallel to the machine direction MD of the web being processed. Therefore, extension in the cross-direction CD at the bonded portions causes the bond sites 50 to rupture and open to form apertures in the web.

One method for forming apertures across the web is to pass the web through nip 131 formed by an incremental stretching system 132 employing opposed pressure applicators 134 and 136 having three-dimensional surfaces which at least to a degree are complementary to one another. Stretching of the laminate web may be accomplished by other methods known in the art, including tentoring, or even by hand. However, to achieve even strain levels across the web, and especially if localized strain differential are desired, the incremental stretching system disclosed herein is preferred.

Figure 12:
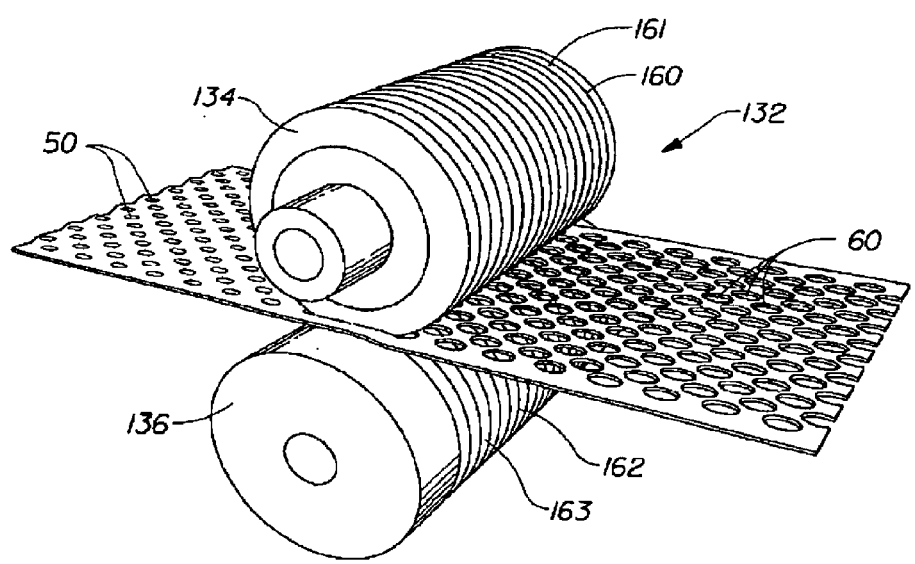
FIG. 12 is a perspective view of an apparatus for stretching a laminate of the present invention to form apertures therein.
Figure 13:
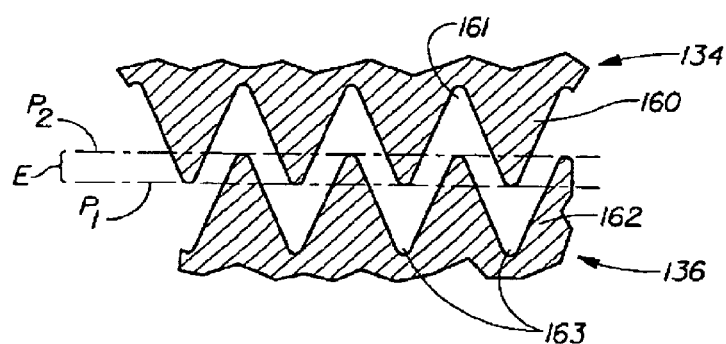
FIG. 13 is a cross-sectional view of a portion of the mating portions of the apparatus shown in FIG. 12.

Referring now to FIG. 12, there is shown a fragmentary enlarged view of the incremental stretching system 132 comprising incremental stretching rollers 134 and 136. The incremental stretching roller 134 includes a plurality of teeth 160 and corresponding grooves 161 which extend about the entire circumference of roller 134. Incremental stretching roller 136 includes a plurality of teeth 162 and a plurality of corresponding grooves 163. The teeth 160 on roller 134 intermesh with or engage the grooves 163 on roller 136, while the teeth 162 on roller 136 intermesh with or engage the grooves 161 on roller 134. The teeth of each roller are generally triangular-shaped, as shown in FIG. 13. The apex of the teeth may be slightly rounded, if desired for certain effects in the finished web.

With reference to FIG. 13, which shows a portion of the intermeshing of the teeth 160 and 162 of rollers 134 and 136, respectively. The term "pitch" as used herein, refers to the distance between the apexes of adjacent teeth. The pitch can be between about 0.02 to about 0.30 inches, and is preferably between about 0.05 and about 0.15 inches. The height (or depth) of the teeth is measured from the base of the tooth to the apex of the tooth, and is preferably equal for all teeth. The height of the teeth can be between about 0.10 inches and 0.90 inches, and is preferably about 0.25 inches and 0.50 inches.

The teeth 160 in one roll can be offset by one-half the pitch from the teeth 162 in the other roll, such that the teeth of one roll (e.g., teeth 160) mesh in the valley (e.g., valley 163) between teeth in the mating roll. The offset permits intermeshing of the two rollers when the rollers are "engaged" or in an intermeshing, operative position relative to one another. In a preferred embodiment, the teeth of the respective rollers are only partially intermeshing. The degree to which the teeth on the opposing rolls intermesh is referred to herein as the "depth of engagement" or "DOE" of the teeth. As shown in FIG. 13, the DOE, E, is the distance between a position designated by plane P1 where the apexes of the teeth on the respective rolls are in the same plane (0% engagement) to a position designated by plane P2 where the apexes of the teeth of one roll extend inward beyond the plane P1 toward the valley on the opposing roll. The optimum or effective DOE for particular laminate webs is dependent upon the height and the pitch of the teeth and the materials of the web.

In other embodiments the teeth of the mating rolls need not be aligned with the valleys of the opposing rolls. That is, the teeth may be out of phase with the valleys to some degree, ranging from slightly offset to greatly offset.

As the laminate web 10 having melt bonded locations 50 passes through the incremental stretching system 132 the laminate web 10 can be subjected to tensioning in the CD or cross-machine direction causing the laminate web 10 to be extended in the CD direction. Alternatively, or additionally the laminate web 10 may be tensioned in the MD (machine direction). The tensioning force placed on the laminate web 10 can be adjusted (e.g., by adjusting DOE) such that it causes the melt bonded locations 50 to separate or rupture creating a plurality of apertures 60 coincident with the melt bonded locations 50 in the laminate web 10. However, portions of the melt bonds of the laminate web 10 remain, as indicated by portions 62 in FIG. 4, thereby maintaining the nonwoven web in a coherent condition even after the melt bonded locations rupture.

After being subjected to the tensioning force applied by the incremental stretching system 132, the laminate web 10 includes a plurality of apertures 60 which are coincident with the melt bonded regions 50 of the laminate web. As mentioned, a portion of the circumferential edges of apertures 60 include remnants 62 of the melt bonded locations 60. It is believed that the remnants 60 help to resist further tearing or delamination of the laminate web.

Figure 14:
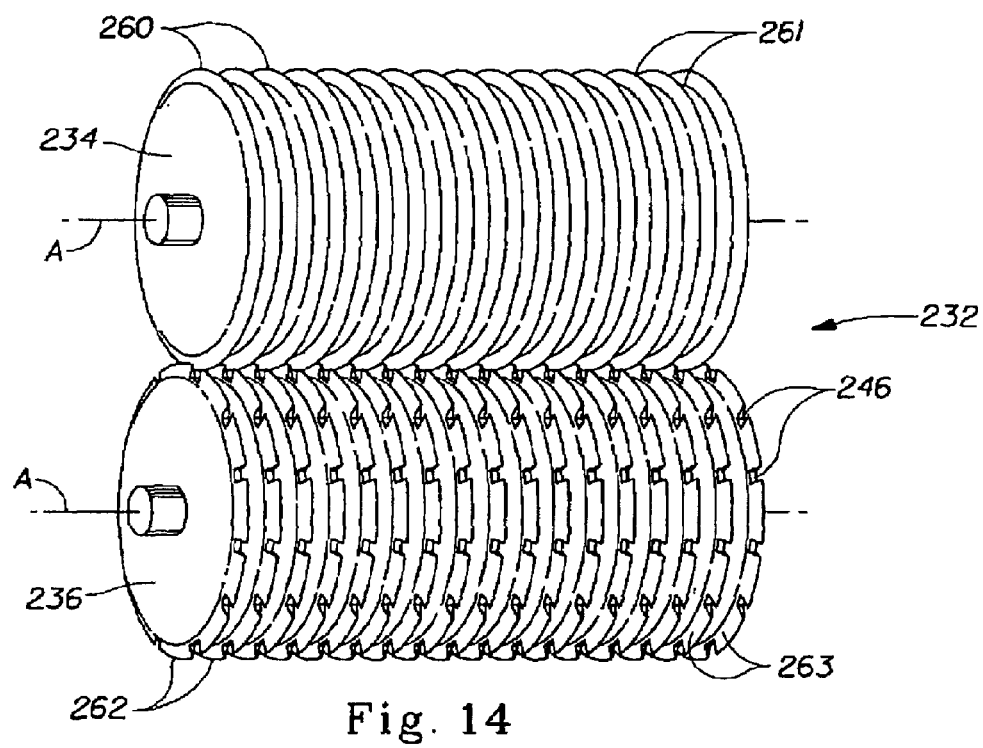
FIG. 14 is a perspective view of an alternative apparatus for stretching a laminate of the present invention in the cross-machine direction to form apertures therein.

Instead of two substantially identical rolls 134 and 136, one or both rolls can be modified to produce extension and additional patterning. For example, one or both rolls can be modified to have cut into the teeth several evenly-spaced thin planar channels 246 on the surface of the roll, as shown on roll 236 in FIG. 14. In FIG. 14 there is shown an enlarged view of an alternative incremental stretching system 232 comprising incremental stretching rollers 234 and 236. The incremental stretching roller 234 includes a plurality of teeth 260 and corresponding grooves 261 which extend about the entire circumference of roller 234. Incremental stretching roller 236 includes a plurality of teeth 262 and a plurality of corresponding grooves 263. The teeth 260 on roller 234 intermesh with or engage the grooves 263 on roller 236, while the teeth 262 on roller 236 intermesh with or engage the grooves 261 on roller 234. The teeth on one or both rollers can have channels 246 formed, such as by machining, such that regions of undeformed laminate web material may remain after stretching. A suitable pattern roll is described in U.S. Pat. No. 5,518,801, issued May 21, 1996, in the name of Chappell, et al., the disclosure of which is incorporated herein by reference.

Figure 15:
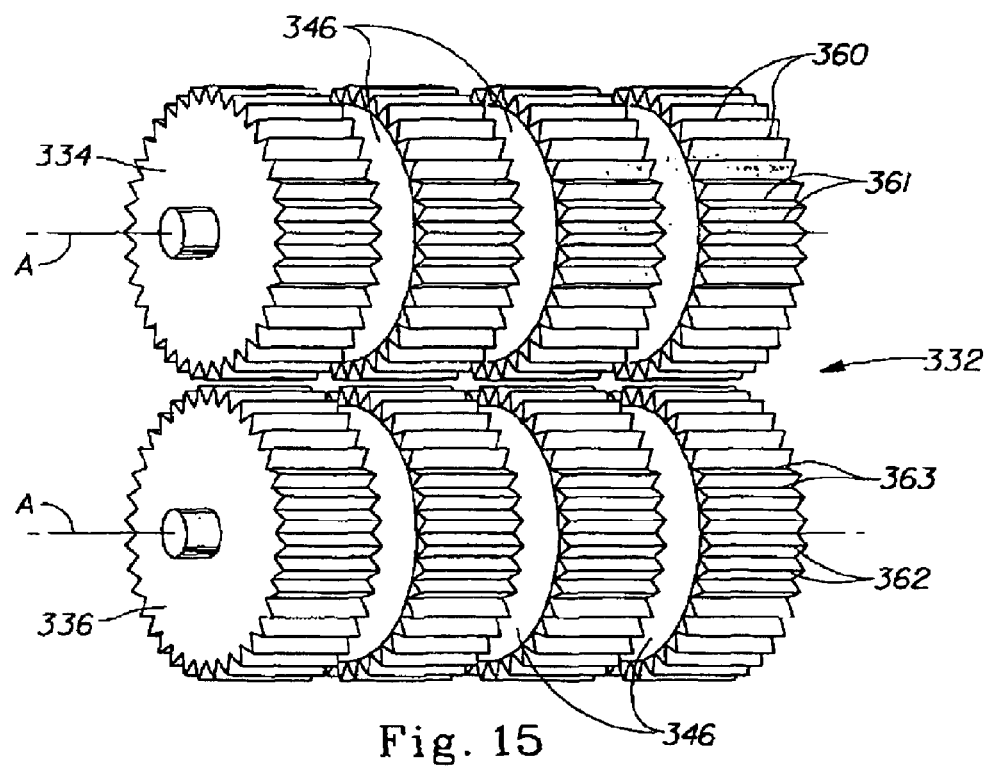
FIG. 15 is a perspective view of another alternative apparatus for stretching a laminate of the present invention in the machine direction to form apertures therein.

Likewise, the incremental stretching can be by mating rolls oriented as shown in FIG. 15. Such rolls comprise a series of ridges 360, 362, and valleys, 361, 363 that run parallel to the axis, A, of the roll, either 334 or 336, respectively. The ridges form a plurality of triangular-shaped teeth on the surface of the roll. Either or both rolls may also have a series of spaced-apart channels 346 that are oriented around the circumference of the cylindrical roll. Rolls as shown are effective in incrementally stretching a laminate having bond sites 50 having the axis 1 oriented generally parallel to the cross-machine (CD) direction of the web as its being processed.

Figure 16:
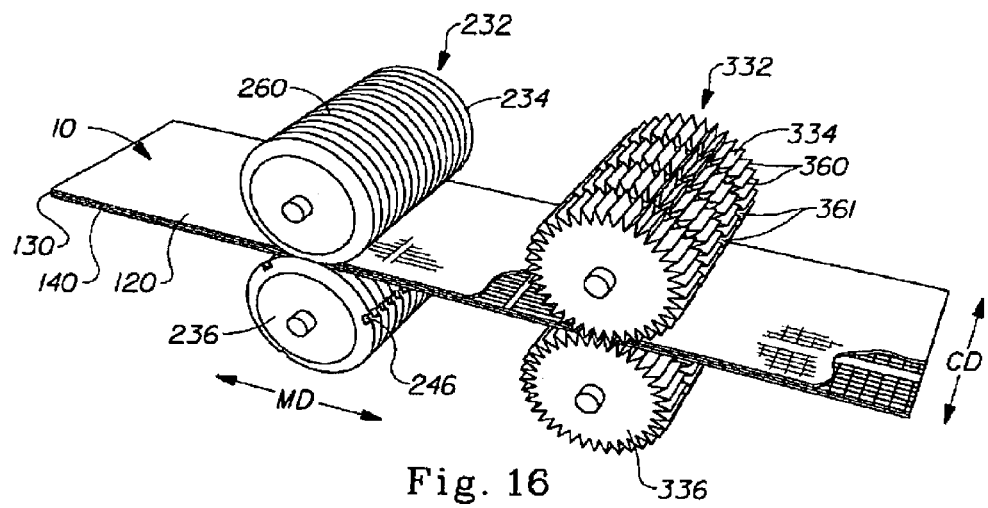
FIG. 16 is a perspective representation of an apparatus for stretching a laminate of the present invention in both the cross-machine and machine directions to form apertures therein.

In one embodiment, the method of the present invention can comprise both CD and MD incremental stretching. As shown in FIG. 16, two pairs of incremental stretching rolls can be used in line, such that one pair (232, which, as shown in FIG. 16 includes a series of spaced-apart channels 246) performs CD stretching, and another pair, 332 performs MD stretching. By this method many interesting fabric-like textures can be made. The resulting hand and visual appearance make such fabric-like webs ideal for use in articles benefiting from a fabric-like look and feel.

EXAMPLES

The following examples are shown in Table 1 as exemplary of the claimed invention. Because the choice of outer and inner layers and combinations is virtually infinite, the examples shown are meant to be illustrative of possible structures, and are not meant to be limiting to any particular material or structure.

In Table 1 various combinations of materials are shown. The layers are numbered in order of structural proximity from one outer layer to the other. Therefore, layer 1 is always an outer layer, and the last numbered layer is likewise an outer layer.

For all the samples shown, the calendaring line speed was 100 feet per minute, but the line speed is not considered critical to the operation of the method. The calendaring pressure was 700 psig for all the samples, but the pressure can be varied as desired as long as bonding is achieved between the outer layers.

To form apertured embodiments of the samples below, the thermally bonded laminate was processed by the incremental stretching process as described above with reference to FIG. 12. For these samples a "Pitch" and depth of engagement ("DOE") are shown.

Clopay films were obtained from Clopay, Cincinnati, Ohio.

Elastomeric formed films are obtained from Tredegar Film Products, Terre Haute, Ind. Such films are an improvement in the aforementioned Radel et al. web as disclosed in the above-mentioned commonly assigned, copending U.S. patent application Ser. No. 08/816,106 entitled Tear Resistant Porous Extensible Web, filed Mar. 14, 1997 in the name of Curro et al. Curro '106 discloses elasticized polymeric webs generally in accordance with the aforementioned Radel et al. patent that may be produced from elastomeric materials known in the art, and may be laminates of polymeric materials. Laminates of this type can be prepared by coextrusion of elastomeric materials and less elastic skin layers and may be used in the body hugging portions of absorbent garments, such as the waistband portions and leg cuffs.

High internal phase emulsion open cell foam materials can be made generally in accordance with the teachings of the above mentioned U.S. Pat. No. 5,260,345 and U.S. Pat. No. 5,268,224.

BBA and Corovin/BBA nonwovens were obtained from BBA, Greenville, S.C.

BOUNTY® paper towels were obtained from The Procter & Gamble Co., Cincinnati, Ohio.

REYNOLD'S metal foil products were obtained from Reynold's Metal Products company.

3M products were obtained from 3M, Minneapolis, Minn.

For the materials shown below, the basis weight is expressed in grams per square meter (gsm). Low density polyethylene is denoted "LDPE"; polypropylene is denoted as "PP"; and polyethylene is denoted as "PE". Spunbond is denoted as "SB".

TABLE 1

Examples of Laminate Webs of the Present Invention

| Example No. | Layer 1 | Layer 2 | Layer 3 | Layer 4 | Layer 5 | Roller Temp. Anvil/Pattern (deg. F.) | Pitch/DOE (inches) |
|---|---|---|---|---|---|---|---|
| 1 | 30 gsm LDPE SB nonwoven from Corovin/BBA | 42 gsm BOUNTY® Paper Towel | 30 gsm LDPE SB nonwoven from Corovin/BBA | | | 250/270 | |
| 2 | 30 gsm LDPE SB nonwoven from Corovin/BBA | 42 gsm BOUNTY® Paper Towel | 42 gsm BOUNTY® Paper Towel | 30 gsm LDPE SB nonwoven from Corovin/BBA | | 250/270 | 0.200/0.300 |
| 3 | 30 gsm LDPE SB nonwoven from Corovin/BBA | 42 gsm BOUNTY® Paper Towel | 30 gsm LDPE SB nonwoven from Corovin/BBA | | | 250/270 | 0.060/0.850 |
| 4 | 80/20 (PE/PP) 30 gsm SB nonwoven from BBA | 23 gsm PE formed film from Clopay | 50/50 (PE/PP) 30 gsm SB nonwoven from BBA | | | 275/295 | |
| 5 | 80/20 (PE/PP) 30 gsm SB nonwoven from BBA | 23 gsm PE formed film from Clopay | 50/50 (PE/PP) 30 gsm SB nonwoven from BBA | | | 275/295 | 0.200/0.300 |
| 6 | 80/20 (PE/PP) 30 gsm SB nonwoven from BBA | 42 gsm BOUNTY® Paper Towel | 23 gsm PE formed film from Clopay | 50/50 (PE/PP) 30 gsm SB nonwoven from BBA | | 275/295 | |
| 7 | 80/20 (PE/PP) 30 gsm SB nonwoven from BBA | 42 gsm BOUNTY® Paper Towel | 23 gsm PE formed film from Clopay | 50/50 (PE/PP) 30 gsm SB nonwoven from BBA | | 275/295 | 0.200/0.300 |
| 8 | 30 gsm LDPE SB nonwoven from Corovin/BBA | M77 spray adhesive from 3 M approx. 13 gsm | REYNOLDS® 65 gsm aluminum foil | M77 spray adhesive from 3 M approx. 13 gsm | 30 gsm LDPE SB nonwoven from Corovin/BBA | 275/295 | 0.060/0.850 |
| 9 | 30 gsm LDPE SB nonwoven from Corovin/BBA | 88 gsm elastomeric formed film from Tredegar | 42 gsm BOUNTY® Paper Towel | 30 gsm LDPE SB nonwoven from Corovin/BBA | | 250/270 | 0.200/0.300 |
| 10 | 30 gsm LDPE SB nonwoven from Corovin/BBA | Spray hot melt adhesive from Ato-Findley approx. 12 gsm | 62 gsm High Internal Phase Emulsion open cell foam | Spray hot melt adhesive from Ato-Findley approx. 12 gsm | 30 gsm LDPE SB nonwoven from Corovin/BBA | 250/270 | 0.200/0.300 |
| 11 | 27 gsm high elongation carded PP nonwoven from BBA | 42 gsm BOUNTY® Paper Towel | 60 gsm laminate of 80/20 50/50 (PE/PP) nonwoven from BBA | | | 295/350 | 0.060/0.110 |

The laminate webs of the present invention may be utilized in many varied applications. For example, the relatively low cost of nonwoven, paper and film materials makes the laminates ideally suited for disposable articles. The articles discussed herein are exemplary of the useful applications for which the laminate of the present invention can be used.

Figure 17:
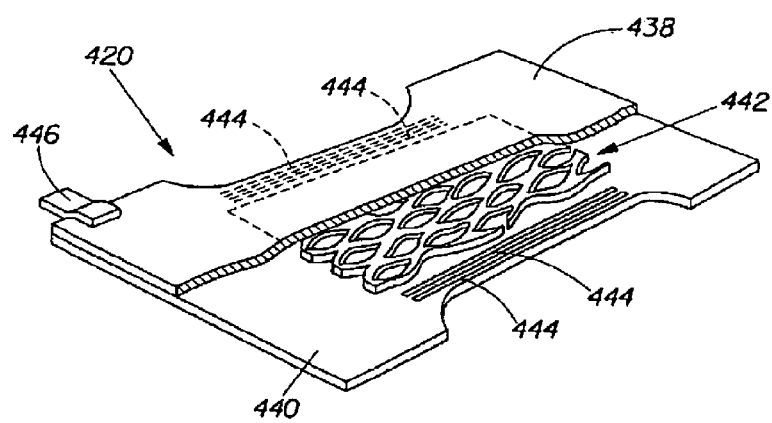
FIG. 17 is a perspective view of a disposable absorbent article having components that can be made of laminate web material of the present invention.

FIG. 17 shows an exemplary embodiment of a disposable diaper 420 in a flat configuration (with all elastic induced contraction removed) with portions of the structure being cut-away to more clearly show the construction. The portion of the diaper which contacts the wearer faces the viewer. The diaper is preferably comprises a liquid pervious topsheet 438; a liquid impervious backsheet 440 joined with the topsheet 438; an absorbent core 442 (shown as an apertured laminate of the present invention) positioned between the topsheet 338 and the backsheet 340; elastic members 344; and tape tab (or mechanical) fasteners 446. The components can be assembled in a variety of well known configurations.

Liquid pervious topsheet 438 could be made of a laminate web like Example 4 (unapertured) or Example 5 (apertured) as shown in Table 1. Backsheet 440 could be made of a laminate webs like Example 4, and absorbent core 442 could be made of a laminate like that of Example 10. Side panels, elastic leg cuffs, and an elastic waist feature can be made of a laminate web like Example 9. Such a laminate exhibits breathability and elasticity, both important in absorbent diapers.

A preferred diaper configuration for a diaper comprising laminates of the present invention is described generally in U.S. Pat. No. 3,860,003, issued Jan. 14, 1975 to Buell. Alternatively preferred configurations for disposable diapers are also disclosed in U.S. Pat. No. 4,808,178 (Aziz et al.); U.S. Pat. No. 4,695,278 (Lawson); U.S. Pat. No. 4,816,025 (Foreman); U.S. Pat. No. 5,151,092 (Buell et al.), all of which are hereby incorporated herein by reference.

In addition to disposable diapers, various embodiments of laminates of the present invention are useful for topsheets, backsheets, and cores in other disposable absorbent articles, such as catamenials, panty liners, pull-up diapers, adult incontinence products, and the like.

Laminates of the present invention can also be useful as wipes, including wet wipes, shop wipes, facial wipes, and the like. For example, Example 3 having an absorbent cellulosic layer as central layer 30 would be an excellent wipe for picking up spills and particulate matter that can be captured in the apertures. Likewise, Example 6, having a polyethylene film would be an excellent wipe for harsh jobs requiring a more durable wipe having extra scrubbing capability. A laminate of the present invention can be considered a durable or semi-durable rag or sponge for most purposes.

Because of the virtually infinite variety of patterns achievable by the method of the present invention, laminates of the present invention can find use as components in home furnishings, including drapes and upholstery. For example, very lacy, sheer patterns can be made that are attractive as window coverings. The colors can be varied easily by varying the component materials, including central layer 30. Higher basis weight materials can be made durable for seat coverings, particularly disposable seat coverings useful in airplanes, buses, and the like.

Laminates of the present invention can be useful as disposable bibs. Example 6 in Table 1, for example, having a polyethylene layer would serve as an effective bib. Even apertured versions, depending on the size of the apertures can be useful as bibs, as the apertures tend to capture food particles better. After use as a bib the bib can be used as a wipe to clean up the baby's surroundings after eating.

Metal-containing webs of the present invention can be used in electrical applications. For example, Example 8 in Table 1 can be used in applications requiring electrical shielding and a soft, compliant carrier material. A laminate similar to Example 8 may find use as a component in circuit boards, electrical cabling, and the like.

Other uses for laminates of the present invention include filters, medical dressings, textured wall coverings, mats and throws, mop heads for dry or wet mops, and geo-textiles.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A laminate web having a plurality of apertures, said laminate web comprising:

(a) a first extensible web comprising a material selected from the group consisting of nonwoven, polymeric film, and combinations thereof, having a first elongation to break;

(b) a second extensible web comprising a material selected from the group consisting of nonwoven, polymeric film, and combinations thereof, joined to said first extensible web at a plurality of bond sites, the second extensible web having a second elongation to break; and (c) a third web material disposed between and not thermally bonded to said first and second extensible webs, said third material having a third elongation to break which is less than both of said first or second elongations to break, and said third material being apertured in regions coincident said bond sites;

wherein said first and second extensible webs of said laminate web are apertured at said bond sites and said bond site has an aspect ratio greater than about 3.

2. The laminate web of claim 1, wherein said laminate is joined by bonds in the absence of adhesive.

3. The laminate web of claim 1, wherein said bond sites are discrete thermal bonds.

4. The laminate web of claim 1, wherein said first or second extensible web comprises a nonwoven.

5. The laminate web of claim 1, wherein said first and second extensible webs are identical.

6. The laminate web of claim 1, wherein said third web material is selected from the group consisting of cellulosic tissue paper, metal foil, open cell foam, paper, paper towels, and combinations thereof.

7. A laminate web having a plurality of apertures, said laminate web comprising:

(a) a first and second webs comprising a material selected from the group consisting of nonwoven, polymeric film, and combinations thereof, being joined and apertured at a plurality of discrete bond sites having an aspect ratio greater than about 3;

(b) a third material disposed between and not thermally bonded to said first and second webs; and (c) the first and second webs being in fluid communication via the apertures and having distinct regions being differentiated by at least one property selected from the group consisting of basis weight, fiber orientation, thickness, and density.

8. The laminate web of claim 7, wherein said laminate is joined by bonds in the absence of adhesive.

9. The laminate web of claim 7, wherein said bond sites are discrete thermal bonds.

10. The laminate web of claim 7, wherein said first or second web comprises a nonwoven.

11. The laminate web of claim 7, wherein said first and second webs are identical.

12. The laminate web of claim 7, wherein said third material comprises cellulosic tissue paper.

13. The laminate web of claim 7, wherein said third material comprises metal foil.

14. The laminate web of claim 7, wherein said third material is an open cell foam.

15. A disposable absorbent article comprising a laminate web having a plurality of apertures, said laminate web comprising:

a) first and second extensible webs being joined at a plurality of discrete bond sites;

b) a third material disposed between and not thermally bonded to said first and second nonwoven webs; and c) said first and second nonwoven webs being in fluid communication via the apertures and having distinct regions being differentiated by at least one property selected from the group consisting of basis weight, fiber orientation, thickness, and density.

16. The laminate web of claim 15, wherein said first or second extensible web comprises a nonwoven.

17. The laminate web of claim 15, wherein said third material comprises absorbent gelling material.

18. A laminate web having a plurality of apertures, said laminate web comprising:

(a) a first web having a first elongation to break;
(b) a second web joined to said first web at a plurality of bond sites, the second web having a second elongation to break; and
(c) a third web material disposed between and not thermally bonded to said first and second webs, said third material having a third elongation to break which is less than both of said first or second elongations to break, and said third material being apertured in regions coincident said bond sites.

* * * * *